US010017790B2

(12) United States Patent
Sporleder et al.

(10) Patent No.: US 10,017,790 B2
(45) Date of Patent: Jul. 10, 2018

(54) WHOLE-CELL BIOTRANSFORMATION OF FATTY ACIDS TO OBTAIN FATTY ALDEHYDES SHORTENED BY ONE CARBON ATOM

(75) Inventors: Fenja Sporleder, Frankfurt am Main (DE); Markus Buchhaupt, Niederdorfelden (DE); Jens Schrader, Frankfurt am Main (DE)

(73) Assignee: SYMRISE AG (DE)

( * ) Notice: Subject to any disclaimer, the term of this patent is extended or adjusted under 35 U.S.C. 154(b) by 652 days.

(21) Appl. No.: 13/818,680

(22) PCT Filed: Aug. 26, 2011

(86) PCT No.: PCT/EP2011/064762
§ 371 (c)(1),
(2), (4) Date: Feb. 24, 2013

(87) PCT Pub. No.: WO2012/025629
PCT Pub. Date: Mar. 1, 2012

(65) Prior Publication Data
US 2013/0149756 A1 Jun. 13, 2013

Related U.S. Application Data

(60) Provisional application No. 61/377,237, filed on Aug. 26, 2010.

(30) Foreign Application Priority Data

Aug. 26, 2010 (DE) .................... 10 2010 039 833

(51) Int. Cl.
C12P 7/24 (2006.01)
C12N 9/02 (2006.01)
C12N 15/09 (2006.01)

(52) U.S. Cl.
CPC .............. *C12P 7/24* (2013.01); *C12N 9/0069* (2013.01); *C12N 9/0071* (2013.01)

(58) Field of Classification Search
CPC ................................ C12P 7/24; C12P 9/0006
USPC .... 435/132, 147, 148, 252.2, 252.33; 3/132, 3/147, 148, 252.2, 252.33
See application file for complete search history.

(56) References Cited

U.S. PATENT DOCUMENTS 5,464,761 A 11/1995 Muller et al.
7,491,854 B2 2/2009 Binder

FOREIGN PATENT DOCUMENTS

| DE | 102004038054 A1 | 3/2006 |
| DE | 102005043152 A1 | 3/2007 |
| DE | 102009007272 A1 | 8/2010 |
| EP | 1244364 B1 | 8/2005 |
| JP | H02200192 A | 8/1990 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Terpe et al. Appl Micrio. Biotec. 2006, 72 pp. 211-222.*
Bannenberg et al. Plant Physiol 2009, 151 pp. 1421-1432.*
Saffert A. et al., A Dual Function α-Dioxygenase-Peroxidase and NAD[+] Oxidoreductase Active Enzyme from Germinating Pea Rationalizing α-Oxidation of Fatty Acids in Plants[1,2] Plant Physiology, Aug. 2000, vol. 123, pp. 1545-1551.
Hamberg M. et al., "α-Oxidation of Fatty Acids in Higher Plants", The Journal of Biological Chemistry, vol. 274, No. 35, Issue of Aug. 27, pp. 24503-24513, 1999.
"Plant Peroxidases", Methods Enzymol, 1955, pp. 801-813.
Smith T. F., Waterman, M.S., "Identification of Common Molecular Subsequences", Journal of Molecular Biology, vol. 147, 1981, pp. 195-197.
International Preliminary Report on Patentability Chapter I, dated Feb. 26, 2013, for priority application PCT/EP2011/064762.
Written Opinion of the International Search Authority, dated Feb. 26, 2013, for priority application PCT/EP2011/064762.
Search Report, dated Jun. 9, 2011, for priority application DE 10 2010 039 833.0.
International Search completed dated Jan. 23, 2012 for priority application PCT/EP2011/064762.
Written Opinion dated Feb. 7, 2012 for priority application PCT/EP2011/064762.
Hamberg et al: "Alpha-Dioxygenases", Biochemical and Biophysical Research Communications, Bd. 338, 2005, Seiten 169-174, XP027218277.
Hamberg et al: "Fatty acid alpha-dioxygenases", Prostaglandins & Other Lipid Mediators, Bd. 68-69, 2002, Seiten 363-374, XP004380634.
Database Protein [Online] Jun. 8, 2010 (Jun. 8, 2010), "Os12g0448900 [Oryza sativa Japonica Group]", XP002667560, gefunden im NCBI Database accession No. NP_001066718.
Koeduka et al: "Catalytic properties of rice alpha-oxygenase", The Journal of Biological Chemistry, Bd. 277, 2002, Seiten 22648-22655, XP002667636.
Kaehne et al: "A recombinant alpha-dioxygenase from rice to produce fatty aldehydes using *E. coli*", Applied Microbiology and Biotechnology, Bd. 90, Feb. 24, 2011 (Feb. 24, 2011), Seiten 989-995, XP002667333.
Database Protein, Online, GenBank AAF64042.2, "Fatty acid alpha-oxidase", [Oryza sativa], Mar. 19, 2007.
Koeduka, T. et al., "Molecular characterization of fatty acid α-hydroperoxide-forming enzyme (α-oxygenase) in rice plants," Biochemical Society Transactions (2000), vol. 28, Part 6, pp. 765-768.

* cited by examiner

*Primary Examiner* — Robert B Mondesi
*Assistant Examiner* — Mohammad Y Meah
(74) *Attorney, Agent, or Firm* — Polsinelli PC; Robert James Balls; Christopher M. Cabral

(57) ABSTRACT

The present invention relates to the area of producing aliphatic aldehydes with 5 to 31 carbon atoms, in particular by microbial conversion of corresponding aliphatic fatty acids with 6 to 32 carbon atoms. The invention also relates to enzymes for catalyzing a conversion reaction of this type and nucleic acids coding for this.

19 Claims, No Drawings

WHOLE-CELL BIOTRANSFORMATION OF FATTY ACIDS TO OBTAIN FATTY ALDEHYDES SHORTENED BY ONE CARBON ATOM

CROSS-REFERENCE TO RELATED APPLICATIONS

This application is a US National Stage of International Application No. PCT/EP2011/064762, filed 26 Aug. 2011, which claims the benefit of U.S. 61/377,237, filed 26 Aug. 2010 and DE 102010039833.0, filed 26 Aug. 2010, all herein fully incorporated by reference.

SEQUENCE LISTING

The Sequence Listing provided herein both via the appended listing and the uploaded sequence listing (txt) file is herein fully incorporated by reference.

The present invention relates to the area of producing aliphatic aldehydes with 5 to 31 carbon atoms, in particular by microbial conversion of corresponding aliphatic fatty acids with 6 to 32 carbon atoms. The invention also relates to enzymes for catalysing a conversion reaction of this type and nucleic acids coding for this.

The enzymatic production of aldehydes is basically already known. Thus, Muller et al. in U.S. Pat. No. 5,464,761 inter alia describe the production of aliphatic aldehydes made of linoleic acid. Also known is the production of C6-C10 aldehydes made of unsaturated triacylglycerides (EP 1244364 B1) by means of lipoxygenases, but aldehyde mixtures are produced in this case.

Binder described in "Enzymatic method of making aldehydes from fatty acids", 2009, Archer Daniels Midland Company, the conversion of plant and animal fats to form the corresponding aldehydes by a fatty acid reductase. However, this conversion depends on co-factors to activate the fatty acid by the formation of acyl-AMP and is therefore difficult to carry out to a production scale instead of to a laboratory scale.

Saffert et al. describe in "A dual function alpha-dioxygenase-peroxidase and NAD(+) oxidoreductase active enzyme from germinating pea rationalizing alpha-oxidation of fatty acids in plants", Plant Physiol, 2000, 1545-52, the conversion of hexadecanoic acid to 2-hydroperoxyhexadecanoic acid and 2-hydroxyhexadecanoic acid by a purified alpha-dioxygenase and, in the process, pentadecanoic acid, and, slightly, pentadecanal were observed as by-products.

Known furthermore is the conversion of linolenic acid, linoleic acid and oleic acid to form the corresponding hydroxy acids and the fatty acids correspondingly shortened by 1 carbon atom and aldehydes (Hamberg et al., "alpha-oxidation of fatty acids in higher plants". J Biol Chem 1999, 24503-24513) and in this case the conversion took place with a protein crude extract from insect cells, which heterologously expressed a pathogen-inducible oxygenase ("PIOX").

However, it is disadvantageous in conventional methods that enzymes isolated from cells and optionally purified have to be used therein. This makes the methods laborious, in that they require additional steps to isolate and optionally purify the respective enzyme, and further measures are required to stabilise the isolated and/or purified enzyme. In a large scale method, the isolated and/or purified enzyme would additionally have to be immobilised, or mechanisms would have to be provided to recover the enzyme from the reaction batch after carrying out the conversion. It is furthermore disadvantageous that, as described above, in some cases, cofactors are required to provide reduction equivalents (NAD(P)H) and/or to provide energy (ATP), so the requirements for adhering to optimal reaction conditions, or at least ones that can be used on a large scale, are additionally complicated.

U.S. Pat. No. 7,491,854 B2 shows a whole cell biotransformation method for producing aldehydes from fatty acids. In this case, oleic acid is converted by E. coli cells, which heterologically express a Nocardia carboxylic acid reductase, for a cultivation period of 24 hours inter alia to the corresponding aldehyde. For a corresponding in vitro conversion, ATP and NADPH were required as co-factors. The conversion in a whole cell biotransformation method can therefore also only be carried out with growing cells, which can accordingly form ATP and NADPH. This also results in the fact that a part of the fatty acid used is metabolised by the growing cells, for example in the framework of the beta-oxidation and is therefore not available for producing an aldehyde.

It is furthermore disadvantageous that during a conversion with a carboxylic acid reductase as described in U.S. Pat. No. 7,491,854 B2, the chain length of the fatty acid is also the chain length of the aldehyde. Many economically interesting aldehydes have an odd number of carbon atoms; fatty acids with an odd number of carbon atoms are, however, generally significantly more expensive than the next longest or next shortest even numbered fatty acids.

It was therefore the object of the present invention to remedy the above-described drawbacks and to disclose a method for producing aldehydes from fatty acids. Furthermore, nucleic acids, enzymes and microorganisms are to be provided to carry out a method of this type.

According to the invention, a method for producing an aldehyde with 5 to 31 carbon atoms is therefore provided, comprising the steps:
a) providing microorganism cells containing a dioxygenase,
b) applying a conversion medium containing a fatty acid with 6 to 32 carbon atoms to the microorganism cells, and
c) converting the fatty acid to the aldehyde by means of the dioxygenase.

Surprisingly, it has been found that even when using intact microorganism cells, such as, for example, E. coli to an economically significant extent, fatty acids are transported into the microorganism cells, without being fed directly to the beta-oxidation. Previously, it was expected that fatty acids are mainly transported by an acyl-CoA synthetase through the inner cell membrane. This enzyme, however, converts the fatty acid to be transported to the corresponding CoA thioester, so this fatty acid transport is energy-consuming for the microorganism cell; on the other hand, CoA fatty acid thioesters are directly fed to the beta-oxidation and correspondingly degraded in growing cells, so no usable aldehyde is formed. Surprisingly, it has now been found that, for example, in E. coli, a second fatty acid transport path has to be available apart from the transport path brought about by the acyl-CoA synthetase, with which fatty acids can also be absorbed by, for example, resting cells and made accessible for the dioxygenase.

It is therefore now also possible in economically relevant methods, in other words beyond the laboratory scale, to produce aldehydes from corresponding fatty acids by a biotransformation, without in the process having to resort to an energy-rich CoA coenzyme and to correspondingly supply energy to the respective microorganism cell, for example by beta oxidative degradation of the fatty acid.

The method according to the invention thus also avoids the necessity for cell disruption and purification of the dioxygenase. The drawback in cell disruption would, in particular, be that a complex medium is produced here, in which the most varied, hardly controllable reactions run and from which the product recovery is unnecessarily complicated. On the other hand, in a whole cell biotransformation according to the invention, the microorganisms used can be readily separated from the surrounding medium. In addition, after separation from the surrounding medium, they can be fed to a further biotransformation batch, so the recovery of the dioxygenase is significantly simplified in comparison to a corresponding method using an isolated and/or purified enzyme and has lower costs. Moreover, the product, in other words the corresponding aldehyde, with suitable running of the method, is delivered to the medium, so the product is more easily accessible for purification.

In the sense of the present invention, a microorganism cell is a cell with an intact cell membrane; the microorganism cells used according to the invention can thus be allowed to grow using conventional cultivation methods and used in this form, without additional perforation of the cell membrane.

A dioxygenase in the sense of the present invention is an enzyme, which catalyses the conversion of a carboxylic group with $O_2$. Particularly preferred and constantly at least also intended for the purposes of the present invention are alpha-dioxygenases. These catalyse the conversion of a carboxylic acid according to the following plan:

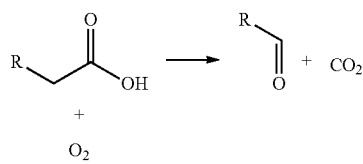

wherein R stands for the radical of the fatty acid. Alpha-dioxygenases therefore catalyse the conversion of a fatty acid into a corresponding aldehyde shortened by 1 C-atom.

The fatty acids converted in a method according to the invention are preferably aliphatic fatty acids. They may be branched or unbranched. Furthermore, they may be saturated or unsaturated. They may furthermore be unsaturated or saturated and carry 1 to 5 substituents here, the substituents in each case being independently selected from hydroxy, C1-C10-alkyl, C1-C10-alkoxy, C6-C10-aryl, phenyl-C1-C5-alkyl and phenyl-C1-C5-alkenyl, wherein the alpha-C atom of the fatty acid does not carry any such substituent.

The fatty acid for forming the aldehyde is preferably selected from:

| Fatty acid | For the formation of |
|---|---|
| n-heptanoic acid | n-hexanal |
| n-nonanoic acid | n-octanal |
| n-decanoic acid | n-nonanal |
| n-undecanoic acid | n-decanal |
| n-dodecanoic acid | n-undecanal |
| n-tridecanoic acid | n-dodecanal |
| n-tetradecanoic acid | n-tridecanal |
| n-hexadecanoic acid | n-pentadecanal |
| 3-methyl-undecanoic acid | 2-methyldecanal |
| 3-methyl-dodecanoic acid | 2-methylundecanal |
| trans-3-heptenoic acid | trans-2-hexenal |
| cis-5-octanoic acid | cis-4-heptenal |
| 3,7-dimethyl-6-octenoic acid | 2,6-dimethyl-5-hepten-1-al |
| 11-dodecenoic acid | 10-undecenal |
| 3,7,11-trimethyl-6,10-dodecadienoic acid | 2,6,10-trimethyl-5,9-undecadienal |
| 4,8-dimethyl-7-nonen-1-acid | citronellal |
| n-heptadecanoic acid | n-hexadecanal |
| n-octadecanoic acid | n-heptadecanal |
| n-nonadecanoic acid | n-octadecanal |

For the purposes of the present invention, the following fatty acids are, in particular, preferred:

| Fatty acid | Associated aldehyde |
|---|---|
| n-hexadecanoic acid (palmitic acid) | n-pentadecanal |
| n-tetradecanoic acid (myristic acid) | n-tridecanal |
| n-dodecanoic acid (lauric acid) | n-undecanal |
| n-decanoic acid (capric acid) | n-nonanal |

The use of an alpha-dioxygenase thus, in an advantageously simple manner, allows the production of an aldehyde with a chain length reduced by 1 carbon atom in relation to the fatty acid used. Therefore, this method is particularly suitable for producing aldehydes with an odd numbered carbon backbone. Accordingly, the associated aldehydes with an odd number of carbon atoms in the chain backbone can be formed from economically obtainable fatty acids with an even number of carbon atoms in the fatty acid backbone.

The method according to the invention may also be carried out in such a way that a plurality of various fatty acids can be simultaneously provided for conversion by the dioxygenase.

A method according to the invention, in particular one with an alpha-dioxygenase is carried out with microorganism cells of the type, in which at least in step c) and preferably also in step b), the beta-oxidation is reduced in comparison to a wild-type strain. This may, for example, take place by administering a beta-oxidation inhibitor to the microorganisms before step c) or simultaneously with step b).

However, preferred according to the invention is a method of the type in which non-growing, resting microorganism cells are used. Accordingly, it is preferred if the medium in step b) has a maximum content of 0.1 ppm of nitrogen compounds and the content of the medium of nitrogen-containing compounds is preferably at most 0.01 ppm and particularly preferably at most 0.001 ppm. Accordingly preferred, is a method according to the invention, in which the medium in step b) does not have any nitrogen source that can be used for the microorganism cells.

A preferred conversion medium for carrying out a method according to the invention therefore consists of water, one or more fatty acid(s) to be converted, optionally a nitrogen-free solubilizer for the fatty acid(s), optionally a nitrogen-free pH buffer and optionally a nitrogen-free nutrient substrate for the microorganism cells. Preferred as pH buffers are sodium and/or potassium phosphate buffers; glucose or another substance that can be metabolised by the microorganism cells is preferred as the nutrient substrate if this substance, compared with the fatty acid(s) to be converted, is preferably metabolised. In this case, "preferably metabolised" means that by adding the substance to the conversion medium, with otherwise unchanged conversion conditions, the quotient of the concentrations of
a) desired aldehyde to fatty acid to be converted, or
b) if a plurality of fatty acids are to be converted, of all the desired aldehydes to all the desired fatty acids,
at least remains the same.

A solubilizer which is preferred according to the invention for fatty acids is dimethyl sulfoxide (DMSO) and Triton X 100.

Preferred for the purposes of the present invention is, in particular, an alpha-dioxygenase with a peroxidase activity of at most 0.4 nkat/mg measured with a chromato-focused, purified enzyme with 2-hydroperoxypalmitic acid and spectro-photometric determination of the oxidation product of guaiacol at 470 nm. This determination method is known to the person skilled in the art, for example, from Maehly, "Plant peroxidases", Methods Enzymol (1955), 801 to 813. The peroxidase activity is particularly preferably at most 0.3 nkat/mg; quite particularly preferably, the dioxygenase has no peroxidase activity that can be shown in this way.

In a method according to the invention, the dioxygenase preferably has an amino acid sequence similarity to the amino acid sequence SEQ ID No. 1 of at least 80%, preferably at least 88%, more preferably at least 93% and particularly preferably at least 98%. In the sense of the present invention, amino acid sequence similarities are determined with the aid of the Waterman-Smith algorithm with a gap open penalty of 10, a gap extension penalty of 0.5 and the Blosum62 matrix. The Waterman-Smith algorithm is described in Smith, T. F. and Waterman, M. S., "Identification of common molecular subsequences", Journal of Molecular Biology (1981), 147: 195 to 197 and, for example, implemented on-line by means of the corresponding tool page of the EMBL, currently "EMBOSS::water" obtainable via www.ebi.ac.uk/tools/emboss/align/. The dioxygenases satisfying these boundary conditions, for the purposes of the method according to the invention, have good activity for converting fatty acids to corresponding aldehydes shortened by 1 carbon atom. They can be expressed well in a large number of microorganisms for a whole cell biotransformation method of the type according to the invention. Corresponding dioxygenases are already known. Their usability for producing aldehydes in a whole cell biotransformation method according to the present invention was, however, unknown.

A method according to the invention is particularly preferred, in which the dioxygenase is an alpha-dioxygenase from a plant of the genus *Oryza*, preferably from rice (*Oryza sativa*). Alpha-dioxygenases of this type are, for example, known from Koeduka et al., "Catalytic properties of rice alpha-oxygenase", J. Biol. Chem. 2002, 22648 to 22655. Alpha-dioxygenases of this type, in particular from rice can be heterologously expressed in *E. coli* easily and with good stability and activity. It is particularly advantageous that they do not have any noteworthy peroxidase activity. Preferred according to the invention is, accordingly, an alpha-dioxygenase with an amino acid sequence according to SEQ ID No. 1.

Further particularly preferred is a method according to the invention, in which the microorganism cells are selected from
the class of gamma proteobacteria, preferably of the family of enterobacteriaceae and particularly preferably from the genera *Escherichia* (in turn particularly preferred therein, *Escherichia coli*),
the class of bacilli, preferably therein of the genus *bacillus* or the order of lactobacillales, and
the class of saccharomycetes, particularly preferably here the family of saccharomycetaceae and dipodascaceae, and particularly preferably the genera saccharomyces and *Yarrowia*.

Particularly preferably, the microorganism cells, in a method according to the invention, are those of the genus *Escherichia*, in particular *Escherichia coli* is particularly preferred. Microorganisms of this type can be handled particularly easily and safely; handling them is also well established on a large scale, and good yields can be achieved therewith.

Accordingly preferred is a method according to the invention for producing an aldehyde with 5 to 31 carbon atoms, comprising the steps:
a) providing *E. coli* cells containing a dioxygenase with a similarity as described above of at least 98% to an amino acid sequence according to SEQ ID No. 1,
b) applying a conversion medium containing a fatty acid with 6 to 32 carbon atoms to the microorganisms, the medium having a content of nitrogen compounds of less than 0.1 ppm and optionally containing glucose, and
c) converting the fatty acid to the corresponding aldehyde with a carbon backbone reduced by 1 carbon atom.

The pH of a conversion medium is adjusted according to the invention preferably with potassium phosphate—to a value of preferably 6.5 to 9, more preferably 7 to 8, and particularly preferably 7.3 to 7.7. These pH values allow good conversions (mmol aldehyde per mmol fatty acid, time and cubic meter conversion medium) to be achieved in particular when using an alpha-dioxygenase from rice as described above in nitrogen-limited *E. coli* cells.

It is also preferred to carry out the conversion in step c) at a temperature of 25 to 39° C., preferably from 28 to 32° C. and particularly preferably from 29 to 31° C. These temperatures are, in particular on conventional *E. coli* production strains, adapted to achieve a good conversion with a method according to the invention, as described above.

According to the invention, a production strain is furthermore disclosed, which heterologously expresses a dioxygenase as described above. The production strain is therefore preferably selected from
the class of gamma proteobacteria, preferably of the family of enterobacteriaceae and preferably from the genera *Escherichia* (in turn particularly preferred therein, *Escherichia coli*),
the class of bacilli, preferably therein of the genus *bacillus* or the order of lactobacillales, and
the class of saccharomycetes, particularly preferably here the family of saccharomycetaceae and dipodascaceae, and particularly preferably the genera saccharomyces and *Yarrowia*.

The dioxygenase expressed from the production strain, preferably a microorganism of the type *Escherichia coli*, is preferably an alpha-dioxygenase with a similarity as defined above to the amino acid sequence SEQ ID No. 1 of at least 80%, preferably at least 88% and particularly preferably at least 93%. Using the production strains according to the invention, the advantages described above of the method according to the invention can be realised.

According to the invention, a nucleic acid is furthermore given for the transformation of a microorganism strain to obtain a production strain according to the invention, the nucleic acid comprising a gene, which codes for a dioxygenase with an amino acid sequence similarity to the amino acid sequence SEQ ID No. 1 of at least 80%, preferably at least 88%, more preferably at least 93% and particularly preferably at least 98%, in each case measured as described above, and wherein the gene is heterologous to the remaining nucleic acid. The nucleic acid is preferably a DNA vector, in particular preferably a recombination vector for the stable incorporation of the gene in the genome of a microorganism by recombination, or an episomal vector.

The gene of a nucleic acid according to the invention is preferably codon-optimised for the associated microorganism to be transformed. Particularly preferably, a nucleic acid according to the invention and a production strain according to the invention therefore have a gene with a sequence according to SEQ ID No. 3 and particularly preferably with a sequence according to SEQ ID No. 4. With genes of this type, in particular in *Escherichia coli* production strains, dioxygenases with an amino acid sequence according to SEQ ID No. 1 can be expressed and the advantages connected with the use of this dioxygenase can be realised.

The gene for the expression according to the invention of the dioxygenase can preferably be expressed under the control of an inducible promoter. It can thus be achieved that the dioxygenase expression only takes place shortly before or during the conversion reaction (step c). This avoids a slower cell growth during the culture of the microorganisms used according to the invention. The gene is preferably under the control of a promoter that can be switched with the lac repressor, so by administering, for example, isopropyl-β-D-1-thiogalactopyranoside (IPTG), the expression of the dioxygenase gene can be induced.

The invention will be described in more detail below with the aid of examples, without these being intended to limit the scope of protection of the claims.

EXAMPLE 1

Production of Pentadecanal from n-Hexadecanoic Acid

The cultivation of a preculture of the *E. coli* strain BL21 (DE3) pET-28a αDOX-rice took place in 5 ml LB-medium with 30 µg Kanamycin per ml medium at 37° C. for about 6 h.
LB-Medium:
5 g tryptone
10 g yeast extract
5 g sodium chloride
ad 1 l water
First Phase: Cultivation
For the main culture, 500 ml LB-medium with 30 µg Kanamycin per ml medium in a 2 l shaking flask was inoculated with 1% (v/v) preculture. The cultivation took place at 37° C. up to a $SD_{600nm}$ of 0.6.
Second Phase: Induction and Expression
After reaching this SD, the induction took place using 0.5 mM isopropyl-β-D-thiogalactopyranoside (IPTG) and the corresponding expression took place at a temperature of 22° C. overnight (about 14 h).
Third Phase: Biotransformation
The cell suspension was transferred to a sterile centrifuge vessel and centrifuged at 8000 g and 4° C. for 10 min. The excess medium was removed by decanting and the remaining cell pellet was dissolved for washing in sterile conversion medium. Centrifugation again took place then at 8000 g and 4° C. for 10 min and the conversion medium was also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.
Conversion Medium
200 mM potassium phosphate buffer
0.5% (w/v) glucose
pH 7.5

The biotransformation was carried out in a 300 ml shaking flask with a baffle with a volume of 25 ml. The addition of the substrate hexadecanoic acid took place dissolved in dimethyl sulfoxide (DMSO). For this purpose 100 mM hexadecanoic acid was dissolved in DMSO and 1.25 ml of this solution added to the cell suspension, so a final concentration of 5 mM was achieved in the biotransformation batch. Before adding the hexadecanoic acid, the cell suspension was preheated to 30° C. in the shaking flask in the incubator while shaking.

The biotransformation took place at 30° C. with strong shaking. After about 2 to 3 h, a pentadecanal concentration of 4 mM was achieved. This means that the conversion was 80%.

EXAMPLE 2

Production of Nonanal from n-Decanoic Acid

Cultivation of the preculture, and first and second phase, as described in Example 1.
Third Phase: Biotransformation
The cell suspension was transferred to a sterile centrifuge vessel and centrifuged at 8000 g and 4° C. for 10 min. The excess medium was removed by decanting and the remaining cell pellet was dissolved for washing in sterile conversion medium.
Centrifugation again took place then at 8000 g and 4° C. for 10 min and the conversion medium was also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.
Conversion Medium:
200 mM potassium phosphate buffer
0.5% (w/v) glucose
pH 7.5

The biotransformation was carried out in a 300 ml shaking flask with a baffle with a volume of 25 ml. The addition of the substrate decanoic acid took place dissolved in dimethyl sulfoxide (DMSO). For this purpose 100 mM decanoic acid was dissolved in DMSO and 1.25 ml of this solution added to the cell suspension, so a final concentration of 5 mM was achieved in the biotransformation batch. Before adding the decanoic acid, the cell suspension was preheated to 37° C. in the shaking flask in the incubator while shaking.

The biotransformation took place at 37° C. with strong shaking. The quantity of nonanal formed was not quantitatively determined. The formation of the product was shown qualitatively by means of GC/MS.

EXAMPLE 3

Production of Tridecanal from n-Tetradecanoic Acid

Cultivation of the preculture, and first and second phase, as described in Example 1.
Third Phase: Biotransformation
The cell suspension was transferred to a sterile centrifuge vessel and centrifuged at 8000 g and 4° C. for 10 min. The excess medium was removed by decanting and the remaining cell pellet was dissolved for washing in sterile conversion medium. Centrifugation again took place then at 8000 g and 4° C. for 10 min and the conversion medium was also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.
Conversion Medium:
200 mM potassium phosphate buffer
0.5% (w/v) glucose
pH 7.5

The biotransformation was carried out in a 300 ml shaking flask with a baffle with a volume of 25 ml. The addition of the substrate tetradecanoic acid took place dissolved in dimethyl sulfoxide (DMSO). For this purpose 100 mM tetradecanoic acid was dissolved in DMSO and 1.25 ml of this solution added to the cell suspension, so a final concentration of 5 mM was achieved in the biotransformation batch. Before adding the tetradecanoic acid, the cell suspension was preheated to 37° C. in the shaking flask in the incubator while shaking.

The biotransformation took place at 37° C. with strong shaking. The quantity of tridecanal formed was not quantitatively determined. The formation of the product was shown qualitatively by means of GC/MS.

EXAMPLE 4

Production of Undecanal from n-Dodecanoic Acid

Cultivation of the preculture, and first and second phase, as described in Example 1.
Third Phase: Biotransformation The cell suspension was transferred to a sterile centrifuge vessel and centrifuged at 8000 g and 4° C. for 10 min. The excess medium was removed by decanting and the remaining cell pellet was dissolved for washing in sterile conversion medium. Centrifugation again took place then at 8000 g and 4° C. for 10 min and the conversion medium was also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.
Conversion Medium:
200 mM potassium phosphate buffer
0.5% (w/v) glucose
pH 7.5

The biotransformation was carried out in a 300 ml shaking flask with a baffle with a volume of 25 ml. The addition of the substrate dodecanoic acid took place dissolved in dimethyl sulfoxide (DMSO). For this purpose 100 mM dodecanoic acid was dissolved in DMSO and 1.25 ml of this solution added to the cell suspension, so a final concentration of 5 mM was achieved in the biotransformation batch. Before adding the dodecanoic acid, the cell suspension was preheated to 37° C. in the shaking flask in the incubator while shaking.

The biotransformation took place at 37° C. with strong shaking. The quantity of undecanal formed was not quantitatively determined. The formation of the product was shown qualitatively by means of GC/MS.

EXAMPLE 5

Production of Heptanal from n-Octanoic Acid

Cultivation of the preculture, and first and second phase, as described in Example 1.
Third Phase: Biotransformation The cell suspension was transferred to a sterile centrifuge vessel and centrifuged at 8000 g and 4° C. for 10 min. The excess medium was removed by decanting and the remaining cell pellet was dissolved for washing in sterile conversion medium. Centrifugation again took place then at 8000 g and 4° C. for 10 min and the conversion medium also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.
Conversion Medium:
200 mM potassium phosphate buffer
0.5% (w/v) glucose
pH 7.5

The biotransformation was carried out in a 300 ml shaking flask with a baffle with a volume of 25 ml. The addition of the substrate octanoic acid took place dissolved in dimethyl sulfoxide (DMSO). For this purpose 100 mM octanoic acid was dissolved in DMSO and 1.25 ml of this solution added to the cell suspension, so a final concentration of 5 mM was achieved in the biotransformation batch. Before adding the octanoic acid, the cell suspension was preheated to 37° C. in the shaking flask in the incubator while shaking.

The biotransformation took place at 37° C. with strong shaking. The quantity of heptanal formed was not quantitatively determined. The formation of the product was shown qualitatively by means of GC/MS.

EXAMPLE 6

Production of Pentadecanal from n-Hexadecanoic Acid with Recovery of the Cells

The cultivation of a preculture of the *E. coli* strain BL21 (DE3) pET-28a αDOX-rice took place in 5 ml LB-medium with 30 µg Kanamycin per ml medium at 37° C. for about 6 h.
LB-Medium:
5 g tryptone
10 g yeast extract
5 g sodium chloride
ad 1 l water
First Phase: Cultivation For the main culture, 500 ml LB-medium with 30 µg Kanamycin per ml medium in a 2 l shaking flask with baffles was inoculated with 1% (v/v) preculture. The cultivation took place at 37° C. to a $SD_{600nm}$ of 0.6.
Second Phase: Induction and Expression After reaching this SD, the induction took place with 0.5 mM isopropyl-β-D-thiogalactopyranoside (IPTG) and the subsequent expression took place at a temperature of 22° C. overnight (about 14 h).
Third Phase: Biotransformation The cell suspension was transferred to a sterile centrifuge vessel and centrifuged at 8000 g and 4° C. for 10 min. The excess medium was removed by decanting and the remaining cell pellet was dissolved for washing in sterile conversion medium. Centrifugation again took place then at 8000 g and 4° C. for 10 min and the conversion medium also removed by decanting. Remaining liquid was removed with a sterile pipette and the cell pellet weighed. This produced about 2 g cell wet mass per 500 ml culture. In order to obtain a concentration of 20 g cell wet mass per 1, the pellet was resuspended in 100 ml sterile conversion medium.

Conversion Medium 200 mM potassium phosphate buffer
0.5% (w/v) glucose
pH 7.5

The biotransformation was carried out in a 300 ml shaking flask with a baffle with a volume of 25 ml. The addition of the substrate hexadecanoic acid took place dissolved in dimethyl sulfoxide (DMSO). For this purpose 100 mM hexadecanoic acid was dissolved in DMSO and 1.25 ml of this solution added to the cell suspension, so a final concentration of 5 mM was achieved in the biotransformation batch. Before adding the hexadecanoic acid, the cell suspension was preheated to 30° C. in the shaking flask in the incubator while shaking. Moreover, 1% (w/v) Triton X 100 was added to the biotransformation batch.

The biotransformation took place at 30° C. with strong shaking. After about 3 h, a pentadecanal concentration of 4 mM was reached. In other words the conversion was 80%.

Repetition Third Phase: Biotransformation with Recovered Biocatalyst

For this purpose, the cells were harvested after 3 h at room temperature for 10 min at 5000 g and the supernatant was removed by decanting. The remaining cell pellet was dissolved for washing in conversion medium and then centrifuged again at room temperature for 10 min at 5000 g. The supernatant was removed by decanting and the cell pellet was resuspended in 20 ml conversion medium. A product concentration of 3 mM could be measured in the supernatant, in other words about 75% of the product remains after the centrifugation in the supernatant and can therefore be separated from the biocatalyst.

For the renewed biotransformation, the 20 ml cell suspension was placed in a fresh 300 ml shaking flask with baffles and 1 ml of the above-described substrate solution (100 mM hexadecanoic acid in DMSO) added, so the substrate concentration in the second passage was also about 5 mM again. Moreover, 1% (w/v) Triton X 100 was also added again to the biotransformation batch. A product concentration of 5.5 mM could already be achieved after 1 h in this second passage of the biotransformation. At the time t0=0 h of this second biotransformation, a pentadecanal concentration of 1 mM was measured (these residues remained in the pellet from the first biotransformation despite washing), in other words, a conversion of 80 to 90% could be achieved again in the second passage.

The invention claimed is:

1. A method for producing an aldehyde with 5 to 31 carbon atoms comprising:

providing an intact living transformed *Escherichia coli* microorganism and expressing a heterologous dioxygenase selected from the group consisting of SEQ ID NO: 1, SEQ ID NO: 2 and a dioxygenase that has an amino acid sequence similarity to SEQ ID No. 1 of at least 93%; measured using the Waterman-Smith algorithm with a gap open penalty of 10, a gap extension penalty of 0.5 and the Blosum62 matrix;

applying a conversion medium containing a fatty acid with 6 to 32 carbon atoms to said intact living microorganism, wherein the applied conversion medium has a content of nitrogen compounds of at most 0.1 ppm and optionally has a glucose content of 0% to 1% (w/v), based on the total conversion medium; and cultivating said intact living microorganism in said conversion medium to convert the fatty acid to the aldehyde by means of the dioxygenase in said intact living microorganism, whereby at least about 80% of the fatty acid in the conversion medium is converted to the aldehyde; wherein the intact living microorganism cell is not disrupted during the production process of the aldehyde.

2. The method according to claim 1, wherein the fatty acid used in the conversion medium is selected from the group consisting of:

linear or branched saturated fatty acids;
linear or branched unsaturated fatty acids; and
unsaturated or saturated fatty acids with 1 to 5 substituents, wherein the substituents are in each case selected independently from hydroxy, C1-C10-alkyl, C1-C10-alkoxy, C6-C10-aryl, phenyl-CI-C5-alkyl and phenyl-CI-C5-alkenyl, wherein the alpha-C atom of the fatty acid does not carry any such substituent.

3. The method according to claim 1, wherein the fatty acid and the associated aldehyde obtained are selected from the group consisting of:

| Fatty acid | For the formation of |
|---|---|
| n-hexadecanoic acid | n-pentadecanal; |
| n-tetradecanoic acid | n-tridecanal; |
| n-dodecanoic acid | n-undecanal; |
| n-decanoic acid | n-nonanal; | and mixtures of two or more of said fatty acids to obtain mixtures of the corresponding aldehydes.

4. The method according to claim 1, wherein applying a conversion medium containing a fatty acid with 6 to 32 carbon atoms to said microorganism comprises one or more of:

adjusting the pH of the conversion medium to 6.5 to 9;
the conversion medium has a content of nitrogen compounds of at most 0.1 ppm; and
the conversion medium has a glucose content of 0.25 to 1% (w/v), based on the total conversion medium.

5. The method according to claim 1, wherein a temperature of 25 to 39° C. is maintained during conversion of the fatty acid to the aldehyde by means of the dioxygenase.

6. The method according to claim 1, the fatty acid and the associated aldehyde obtained are selected from the group consisting of:

| Fatty acid | For the formation of |
|---|---|
| n-heptanoic acid | n-hexanal; |
| n-nonanoic acid | n-octanal; |
| n-decanoic acid | n-nonanal; |
| n-undecanoic acid | n-decanal; |
| n-dodecanoic acid | n-undecanal; |
| n-tridecanoic acid | n-dodecanal; |
| n-tetradecanoic acid | n-tridecanal; |
| n-hexadecanoic acid | n-pentadecanal; |
| 3-methyl-undecanoic acid | 2-methyldecanal; |
| 3-methyl-dodecanoic acid | 2-methylundecanal; |
| trans-3-heptenoic acid | trans-2-hexenal; |
| cis-5-octanoic acid | cis-4-heptenal; |
| 3,7-dimethyl-6-octenoic acid | 2,6-dimethyl-5-hepten-1-al; |
| 11-dodecenoic acid | 10-undecenal; |
| 3,7,11-trimethyl-6,10-dodecadienoic acid | 2,6,10-trimethyl-5,9-undecadienal; |
| 4,8-dimethyl-7-nonen-1-acid | Citronellal; |
| n-heptadecanoic acid | n-hexadecanal; |
| n-octadecanoic acid | n-heptadecanal; and |
| n-nonadecanoic acid | n-octadecanal. |

7. The method according to claim 1, wherein applying a conversion medium containing a fatty acid with 6 to 32 carbon atoms to the microorganism cells comprises one or more of:
adjusting the pH of the conversion medium to between 7.3 and 7.7;
adjusting the pH of the conversion medium by an aqueous potassium phosphate buffer with a concentration of between 150 and 400 mM;
the conversion medium has a content of nitrogen compounds of at most 0.001; and
the conversion medium has a glucose content of 0.4 to 0.6% (w/v) based on the total conversion medium.

8. The method of claim 1 wherein said dioxygenase has the amino acid sequence of SEQ ID NO: 1.

9. The method of claim 1 wherein said dioxygenase has the amino acid sequence of SEQ ID NO: 2.

10. The method of claim 1 wherein said dioxygenase has an amino acid sequence similarity to SEQ ID No. 1 of at least 93%; measured using the Waterman-Smith algorithm with a gap open penalty of 10, a gap extension penalty of 0.5 and the Blosum62 matrix.

11. The method of claim 1 wherein said dioxygenase has an amino acid sequence similarity to SEQ ID No. 1 of at least 98%; measured using the Waterman-Smith algorithm with a gap open penalty of 10, a gap extension penalty of 0.5 and the Blosum62 matrix.

12. The method of claim 1, wherein said aldehyde is produced in amounts beyond the laboratory scale.

13. The method of claim 1, wherein said aldehyde is recovered from the medium without perforating the cell membrane of said living organism.

14. The method of claim 1, whereby at least about 90% of the fatty acid in the conversion medium is converted to the aldehyde.

15. The method of claim 1,
wherein the applied conversion medium (i) is maintained at a pH of 6.5 to 9; (ii) has a content of nitrogen compounds of at most 0.1 ppm; and (iii) has a glucose content of 0.25 to 1% (w/v), based on the total conversion medium.

16. The method of claim 15, wherein the applied conversion medium (i) is maintained at a pH of between 7.3 and 7.7; (ii) has a content of nitrogen compounds of at most 0.001; and (iii) has a glucose content of 0.4 to 0.6% (w/v) based on the total conversion medium.

17. The method of claim 1, wherein the conversion medium contains a nitrogen-free solubilizer selected from dimethyl sulfoxide (DMSO) and Triton X-100.

18. The method of claim 17, wherein the conversion medium contains Triton X-100.

19. A method for producing an aldehyde with 5 to 31 carbon atoms comprising cultivating an intact living transformed *Escherichia coli* microorganism expressing a heterologous dioxygenase selected from the group consisting of SEQ ID NO: 1, SEQ ID NO: 2 and a dioxygenase that has an amino acid sequence similarity to SEQ ID No. 1 of at least 93%; measured using the Waterman-Smith algorithm with a gap open penalty of 10, a gap extension penalty of 0.5 and the Blosum62 matrix, in a conversion medium containing (i) a fatty acid with 6 to 32 carbon atoms (ii) a content of nitrogen compounds of at most 0.1 ppm and optionally (iii) a glucose content of 0% to 1% (w/v) based on the total conversion medium to convert the fatty acid to the aldehyde by means of the dioxygenase in said intact living microorganism, whereby at least about 80% of the fatty acid in the conversion medium is converted to the aldehyde; wherein the intact living microorganism cell is not disrupted during the production process of the aldehyde.

* * * * *

SEQUENCE LISTING

```
<160> NUMBER OF SEQ ID NOS: 4

<210> SEQ ID NO 1
<211> LENGTH: 231
<212> TYPE: PRT
<213> ORGANISM: Oryza sativa

<400> SEQUENCE: 1

Gly Pro Ile Leu Gly Gly Leu Val Gly Leu Lys Lys Pro Asn Asn His
1               5                   10                  15

Gly Val Pro Tyr Ser Leu Thr Glu Glu Phe Thr Ser Val Tyr Arg Met
            20                  25                  30

His Ser Leu Ile Pro Ser Thr Leu Lys Leu Arg Asp Pro Thr Gly Gln
        35                  40                  45

Pro Asp Ala Asn Asn Ser Pro Pro Cys Leu Glu Asp Ile Asp Ile Gly
    50                  55                  60

Glu Met Ile Gly Leu Lys Gly Glu Glu Gln Leu Ser Lys Ile Gly Phe
65                  70                  75                  80

Glu Lys Gln Ala Leu Ser Met Gly Tyr Gln Ala Cys Gly Ala Leu Glu
                85                  90                  95

Leu Trp Asn Tyr Pro Ser Phe Phe Arg Asn Leu Ile Pro Gln Asn Leu
            100                 105                 110

Asp Gly Thr Asn Arg Ser Asp Arg Ile Asp Leu Ala Ala Leu Glu Val
        115                 120                 125

Tyr Arg Asp Arg Glu Arg Ser Val Pro Arg Tyr Asn Glu Phe Arg Arg
    130                 135                 140

Arg Leu Phe Leu Ile Pro Ile Lys Ser Trp Glu Asp Leu Thr Ser Asp
145                 150                 155                 160

Lys Asp Ala Ile Glu Thr Ile Arg Ala Ile Tyr Gly Asp Asp Val Glu
                165                 170                 175

Lys Leu Asp Leu Leu Val Gly Leu Met Ala Glu Lys Lys Ile Lys Gly
            180                 185                 190

Phe Ala Ile Ser Glu Thr Ala Phe Asn Ile Phe Ile Leu Met Ala Ser
        195                 200                 205
```

```
Arg Arg Leu Glu Ala Asp Arg Phe Phe Thr Ser Asn Phe Asn Glu Glu
    210                 215                 220
Thr Tyr Thr Lys Lys Gly Met
225                 230

<210> SEQ ID NO 2
<211> LENGTH: 618
<212> TYPE: PRT
<213> ORGANISM: Oryza sativa

<400> SEQUENCE: 2

Met Gly Ser Gly Leu Phe Lys Pro Arg Val His Pro Asp Leu Arg Asp
1               5                   10                  15

Val Phe Ser Lys Met Ser Phe Phe Asp Lys Ile Gly Phe Leu Phe Ile
            20                  25                  30

His Ala Phe Asp Lys Arg Asn Leu Trp His Lys Val Pro Val Pro Ile
        35                  40                  45

Gly Leu Leu Tyr Leu Asn Thr Arg Arg Thr Leu Leu Glu Lys Tyr Asn
    50                  55                  60

Leu Leu Ala Val Gly Arg Ser Ser His Gly Ala Leu Phe Asp Pro Lys
65                  70                  75                  80

Glu Phe Leu Tyr Arg Thr Glu Asp Gly Lys Tyr Asn Asp Pro His Asn
                85                  90                  95

Ala Glu Ala Gly Ser Gln Asn Thr Phe Phe Gly Arg Asn Met Glu Pro
            100                 105                 110

Val Asp Gln Gln Asp Glu Leu Met Ser Pro Asp Pro Phe Val Val Ala
        115                 120                 125

Thr Lys Leu Leu Ala Arg Arg Glu Tyr Lys Asp Thr Gly Lys Gln Phe
    130                 135                 140

Asn Ile Leu Ala Ala Ala Trp Ile Gln Phe Met Val His Asp Trp Met
145                 150                 155                 160

Asp His Met Glu Asp Thr Gly Gln Ile Gly Ile Thr Ala Pro Lys Glu
                165                 170                 175

Val Ala Asn Glu Cys Pro Leu Lys Ser Phe Lys Phe His Pro Thr Lys
            180                 185                 190

Glu Leu Pro Thr Asn Ser Asp Gly Ile Lys Ile Gly His Tyr Asn Ile
        195                 200                 205

Arg Thr Ala Trp Trp Asp Gly Ser Ala Val Tyr Gly Asn Asn Glu Glu
    210                 215                 220

Arg Ala Glu Lys Leu Arg Thr Tyr Val Asp Gly Lys Leu Val Ile Gly
225                 230                 235                 240

Asp Asp Gly Leu Leu Leu His Lys Glu Asn Gly Val Ala Leu Ser Gly
                245                 250                 255

Asp Ile Arg Asn Ser Trp Ala Gly Val Ser Ile Leu Gln Ala Leu Phe
            260                 265                 270

Val Lys Glu His Asn Ala Val Cys Asp Ala Ile Lys Glu Glu His Pro
        275                 280                 285

Asn Leu Ser Asp Glu Glu Leu Tyr Arg Tyr Ala Lys Leu Val Thr Ser
    290                 295                 300

Ala Val Ile Ala Lys Val His Thr Ile Asp Trp Thr Val Glu Leu Leu
305                 310                 315                 320

Lys Thr Lys Thr Met Arg Ala Ala Met Arg Ala Asn Trp Tyr Gly Leu
                325                 330                 335

Leu Gly Lys Lys Ile Lys Asp Thr Phe Gly His Ile Gly Gly Pro Ile
            340                 345                 350
```

```
Leu Gly Gly Leu Val Gly Leu Lys Pro Asn Asn His Gly Val Pro
        355                 360                 365

Tyr Ser Leu Thr Glu Glu Phe Thr Ser Val Tyr Arg Met His Ser Leu
370                 375                 380

Ile Pro Ser Thr Leu Lys Leu Arg Asp Pro Thr Gly Gln Pro Asp Ala
385                 390                 395                 400

Asn Asn Ser Pro Pro Cys Leu Glu Asp Ile Asp Ile Gly Glu Met Ile
                405                 410                 415

Gly Leu Lys Gly Glu Glu Gln Leu Ser Lys Ile Gly Phe Glu Lys Gln
                420                 425                 430

Ala Leu Ser Met Gly Tyr Gln Ala Cys Gly Ala Leu Glu Leu Trp Asn
            435                 440                 445

Tyr Pro Ser Phe Phe Arg Asn Leu Ile Pro Gln Asn Leu Asp Gly Thr
        450                 455                 460

Asn Arg Ser Asp Arg Ile Asp Leu Ala Ala Leu Glu Val Tyr Arg Asp
465                 470                 475                 480

Arg Glu Arg Ser Val Pro Arg Tyr Asn Glu Phe Arg Arg Leu Phe
                485                 490                 495

Leu Ile Pro Ile Lys Ser Trp Glu Asp Leu Thr Ser Asp Lys Asp Ala
                500                 505                 510

Ile Glu Thr Ile Arg Ala Ile Tyr Gly Asp Asp Val Glu Lys Leu Asp
            515                 520                 525

Leu Leu Val Gly Leu Met Ala Glu Lys Lys Ile Lys Gly Phe Ala Ile
        530                 535                 540

Ser Glu Thr Ala Phe Asn Ile Phe Ile Leu Met Ala Ser Arg Arg Leu
545                 550                 555                 560

Glu Ala Asp Arg Phe Phe Thr Ser Asn Phe Asn Glu Glu Thr Tyr Thr
                565                 570                 575

Lys Lys Gly Met Gln Trp Val Lys Thr Thr Glu Gly Leu Arg Asp Val
                580                 585                 590

Ile Asn Arg His Tyr Pro Glu Ile Thr Ala Lys Trp Met Lys Ser Ser
            595                 600                 605

Ser Ala Phe Ser Val Trp Asp Ala Asp Tyr
        610                 615

<210> SEQ ID NO 3
<211> LENGTH: 1854
<212> TYPE: DNA
<213> ORGANISM: Oryza sativa
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
```

-continued

```
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
```

-continued

```
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
```

```
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
```

-continued

```
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
```

-continued

```
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
```

```
-continued

<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
```

```
-continued

<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
```

-continued

```
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
```

```
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
```

-continued

```
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
```

-continued

```
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
```

-continued

```
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
```

-continued

```
<220> FEATURE:
<221> NAME/KEY: misc_feature
<222> LOCATION: (1401)..(1401)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1422)..(1422)
<223> OTHER INFORMATION: n is a, c, g, or t
<220> FEATURE:
<221> NAME/KEY: misc_feature
<222> LOCATION: (1425)..(1425)
<223> OTHER INFORMATION: n is a, c, g, or t
<220> FEATURE:
<221> NAME/KEY: misc_feature
<222> LOCATION: (1431)..(1431)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1443)..(1443)
<223> OTHER INFORMATION: n is a, c, g, or t
<220> FEATURE:
<221> NAME/KEY: misc_feature
<222> LOCATION: (1449)..(1449)
<223> OTHER INFORMATION: n is a, c, g, or t
<220> FEATURE:
<221> NAME/KEY: misc_feature
<222> LOCATION: (1452)..(1452)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t
<220> FEATURE:
<221> NAME/KEY: misc_feature
<222> LOCATION: (1461)..(1461)
<223> OTHER INFORMATION: n is a, c, g, or t
<220> FEATURE:
<221> NAME/KEY: misc_feature
<222> LOCATION: (1476)..(1476)
<223> OTHER INFORMATION: n is a, c, g, or t
<220> FEATURE:
<221> NAME/KEY: misc_feature
<222> LOCATION: (1479)..(1479)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1485)..(1485)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
```

-continued

```
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1506)..(1506)
<223> OTHER INFORMATION: n is a, c, g, or t
<220> FEATURE:
<221> NAME/KEY: misc_feature
<222> LOCATION: (1518)..(1518)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1524)..(1524)
<223> OTHER INFORMATION: n is a, c, g, or t
<220> FEATURE:
<221> NAME/KEY: misc_feature
<222> LOCATION: (1536)..(1536)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1551)..(1551)
<223> OTHER INFORMATION: n is a, c, g, or t
<220> FEATURE:
<221> NAME/KEY: misc_feature
<222> LOCATION: (1554)..(1554)
<223> OTHER INFORMATION: n is a, c, g, or t
<220> FEATURE:
<221> NAME/KEY: misc_feature
<222> LOCATION: (1563)..(1563)
<223> OTHER INFORMATION: n is a, c, g, or t
<220> FEATURE:
<221> NAME/KEY: misc_feature
<222> LOCATION: (1572)..(1572)
<223> OTHER INFORMATION: n is a, c, g, or t
<220> FEATURE:
<221> NAME/KEY: misc_feature
<222> LOCATION: (1581)..(1581)
<223> OTHER INFORMATION: n is a, c, g, or t
<220> FEATURE:
<221> NAME/KEY: misc_feature
<222> LOCATION: (1587)..(1587)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1593)..(1593)
<223> OTHER INFORMATION: n is a, c, g, or t
<220> FEATURE:
<221> NAME/KEY: misc_feature
<222> LOCATION: (1596)..(1596)
<223> OTHER INFORMATION: n is a, c, g, or t
<220> FEATURE:
<221> NAME/KEY: misc_feature
<222> LOCATION: (1599)..(1599)
<223> OTHER INFORMATION: n is a, c, g, or t
<220> FEATURE:
<221> NAME/KEY: misc_feature
<222> LOCATION: (1605)..(1605)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t
```

-continued

```
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1635)..(1635)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t
<220> FEATURE:
<221> NAME/KEY: misc_feature
<222> LOCATION: (1644)..(1644)
<223> OTHER INFORMATION: n is a, c, g, or t
<220> FEATURE:
<221> NAME/KEY: misc_feature
<222> LOCATION: (1662)..(1662)
<223> OTHER INFORMATION: n is a, c, g, or t
<220> FEATURE:
<221> NAME/KEY: misc_feature
<222> LOCATION: (1668)..(1668)
<223> OTHER INFORMATION: n is a, c, g, or t
<220> FEATURE:
<221> NAME/KEY: misc_feature
<222> LOCATION: (1671)..(1671)
<223> OTHER INFORMATION: n is a, c, g, or t
<220> FEATURE:
<221> NAME/KEY: misc_feature
<222> LOCATION: (1674)..(1674)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1686)..(1686)
<223> OTHER INFORMATION: n is a, c, g, or t
<220> FEATURE:
<221> NAME/KEY: misc_feature
<222> LOCATION: (1692)..(1692)
<223> OTHER INFORMATION: n is a, c, g, or t
<220> FEATURE:
<221> NAME/KEY: misc_feature
<222> LOCATION: (1701)..(1701)
<223> OTHER INFORMATION: n is a, c, g, or t
<220> FEATURE:
<221> NAME/KEY: misc_feature
<222> LOCATION: (1704)..(1704)
<223> OTHER INFORMATION: n is a, c, g, or t
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (1728)..(1728)
<223> OTHER INFORMATION: n is a, c, g, or t
<220> FEATURE:
<221> NAME/KEY: misc_feature
<222> LOCATION: (1737)..(1737)
<223> OTHER INFORMATION: n is a, c, g, or t
<220> FEATURE:
<221> NAME/KEY: misc_feature
<222> LOCATION: (1749)..(1749)
<223> OTHER INFORMATION: n is a, c, g, or t
<220> FEATURE:
<221> NAME/KEY: misc_feature
<222> LOCATION: (1755)..(1755)
<223> OTHER INFORMATION: n is a, c, g, or t
```

<220> FEATURE:
<221> NAME/KEY: misc_feature
<222> LOCATION: (1758)..(1758)
<223> OTHER INFORMATION: n is a, c, g, or t
<220> FEATURE:
<221> NAME/KEY: misc_feature
<222> LOCATION: (1764)..(1764)
<223> OTHER INFORMATION: n is a, c, g, or t
<220> FEATURE:
<221> NAME/KEY: misc_feature
<222> LOCATION: (1767)..(1767)
<223> OTHER INFORMATION: n is a, c, g, or t
<220> FEATURE:
<221> NAME/KEY: misc_feature
<222> LOCATION: (1770)..(1770)
<223> OTHER INFORMATION: n is a, c, g, or t
<220> FEATURE:
<221> NAME/KEY: misc_feature
<222> LOCATION: (1776)..(1776)
<223> OTHER INFORMATION: n is a, c, g, or t
<220> FEATURE:
<221> NAME/KEY: misc_feature
<222> LOCATION: (1785)..(1785)
<223> OTHER INFORMATION: n is a, c, g, or t
<220> FEATURE:
<221> NAME/KEY: misc_feature
<222> LOCATION: (1794)..(1794)
<223> OTHER INFORMATION: n is a, c, g, or t
<220> FEATURE:
<221> NAME/KEY: misc_feature
<222> LOCATION: (1803)..(1803)
<223> OTHER INFORMATION: n is a, c, g, or t
<220> FEATURE:
<221> NAME/KEY: misc_feature
<222> LOCATION: (1806)..(1806)
<223> OTHER INFORMATION: n is a, c, g, or t
<220> FEATURE:
<221> NAME/KEY: misc_feature
<222> LOCATION: (1821)..(1821)
<223> OTHER INFORMATION: n is a, c, g, or t
<220> FEATURE:
<221> NAME/KEY: misc_feature
<222> LOCATION: (1824)..(1824)
<223> OTHER INFORMATION: n is a, c, g, or t
<220> FEATURE:
<221> NAME/KEY: misc_feature
<222> LOCATION: (1827)..(1827)
<223> OTHER INFORMATION: n is a, c, g, or t
<220> FEATURE:
<221> NAME/KEY: misc_feature
<222> LOCATION: (1830)..(1830)
<223> OTHER INFORMATION: n is a, c, g, or t
<220> FEATURE:
<221> NAME/KEY: misc_feature
<222> LOCATION: (1836)..(1836)
<223> OTHER INFORMATION: n is a, c, g, or t
<220> FEATURE:
<221> NAME/KEY: misc_feature
<222> LOCATION: (1839)..(1839)
<223> OTHER INFORMATION: n is a, c, g, or t
<220> FEATURE:
<221> NAME/KEY: misc_feature
<222> LOCATION: (1848)..(1848)
<223> OTHER INFORMATION: n is a, c, g, or t

<400> SEQUENCE: 3
atgggnwsng gnytnttyaa rccnmgngtn cayccngayy tnmgngaygt nttywsnaar 60
atgwsnttyt tygayaarat hggnttyytn ttyathcayg cnttygayaa rmgnaayytn 120
tggcayaarg tnccngtncc nathggnytn ytntayytna ayacnmgnmg nacnytnytn 180
garaartaya ayytnytngc ngtnggnmgn wsnwsncayg gngcnytntt ygayccnaar 240
garttyytnt aymgnacnga rgayggnaar tayaaygayc cncayaaygc ngargcnggn 300
wsncaraaya cnttyttygg nmgnaayatg garccngtng aycarcarga ygarytnatg 360

-continued

```
wsnccngayc cnttygtngt ngcnacnaar ytnytngcnm gnmgngarta yaargayacn    420
ggnaarcart tyaayathyt ngcngcngcn tggathcart tyatggtnca ygaytggatg    480
gaycayatgg argayacngg ncarathggn athacngcnc cnaargargt ngcnaaygar    540
tgyccnytna arwsnttyaa rttycayccn acnaargary tnccnacnaa ywsngayggn    600
athaarathg gncaytayaa yathmgnacn gcntggtggg ayggnwsngc ngtntayggn    660
aayaaygarg armgngcnga raarytnmgn acntaygtng ayggnaaryt ngtnathggn    720
gaygayggny tnytnytnca yaargaraay ggngtngcny tnwsnggnga yathmgnaay    780
wsntgggcng gngtnwsnat hytncargcn ytnttygtna argarcayaa ygcngtntgy    840
gaygcnatha argargarca yccnaayytn wsngaygarg arytntaymg ntaygcnaar    900
ytngtnacnw sngcngtnat hgcnaargtn cayacnathg aytggacngt ngarytnytn    960
aaracnaara cnatgmgngc ngcnatgmgn gcnaaytggt ayggnytnyt nggnaaraar   1020
athaargaya cnttyggnca yathggnggn ccnathytng gnggnytngt nggnytnaar   1080
aarccnaaya aycayggngt nccntaywsn ytnacngarg arttyacnws ngtntaymgn   1140
atgcaywsny tnathccnws nacnytnaar ytnmgngayc cnacnggnca rccngaygcn   1200
aayaaywsnc cnccntgyyt ngargayath gayathggng aratgathgg nytnaarggn   1260
gargarcary tnwsnaarat hggnttygar aarcargcny tnwsnatggg ntaycargcn   1320
tgyggngcny tngarytntg gaaytayccn wsnttyttym gnaayytnat hccncaraay   1380
ytngayggna cnaaymgnws ngaymgnath gayytngcng cnytngargt ntaymgngay   1440
mgngarmgnw sngtnccnmg ntayaaygar ttymgnmgnm gnytnttyyt nathccnath   1500
aarwsntggg argayytnac nwsngayaar gaygcnathg aracnathmg ngcnathtay   1560
ggngaygayg tngaraaryt ngayytnytn gtnggnytna tggcngaraa raarathaar   1620
ggnttygcna thwsngarac ngcnttyaay athttyathy tnatggcnws nmgnmgnytn   1680
gargcngaym gnttyttyac nwsnaaytty aaygargara cntayacnaa raarggnatg   1740
cartgggtna aracnacnga rggnytnmgn gaygtnatha aymgncayta yccngarath   1800
acngcnaart ggatgaarws nwsnwsngcn ttywsngtnt gggaygcnga ytay         1854
```

<210> SEQ ID NO 4
<211> LENGTH: 1854
<212> TYPE: DNA
<213> ORGANISM: Oryza sativa

<400> SEQUENCE: 4

```
atgggcagcg gcctgtttaa accgcgcgtg catccggatc tgcgcgatgt gtttagcaaa     60
atgagctttt ttgataaaat tggctttctg tttattcatg cgtttgataa acgcaacctg    120
tggcataaag tgccggtgcc gattggcctg ctgtatctga acacccgccg caccctgctg    180
gaaaaatata acctgctggc ggtgggccgc agcagccatg gcgcgctgtt tgatccgaaa    240
gaatttctgt atcgcaccga agatggcaaa tataacgatc cgcataacgc ggaagcgggc    300
agccagaaca ccttttttgg ccgcaacatg gaaccggtgg atcagcagga tgaactgatg    360
agcccggatc cgtttgtggt ggcgaccaaa ctgctggcgc gccgcgaata taaagatacc    420
ggcaaacagt ttaacattct ggcggcggcg tggattcagt ttatggtgca tgattggatg    480
gatcatatgg aagataccgg ccagattggc attaccgcgc cgaaagaagt ggcgaacgaa    540
tgcccgctga aagctttaa atttcatccg accaaagaac tgccgaccaa cagcgatggc     600
attaaaattg gccattataa cattcgcacc gcgtggtggg atggcagcgc ggtgtatggc    660
```

```
aacaacgaag aacgcgcgga aaaactgcgc acctatgtgg atggcaaact ggtgattggc    720
gatgatggcc tgctgctgca taaagaaaac ggcgtggcgc tgagcggcga tattcgcaac    780
agctgggcgg gcgtgagcat tctgcaggcg ctgtttgtga aagaacataa cgcggtgtgc    840
gatgcgatta aagaagaaca tccgaacctg agcgatgaag aactgtatcg ctatgcgaaa    900
ctggtgacca gcgcggtgat tgcgaaagtg cataccattg attggaccgt ggaactgctg    960
aaaaccaaaa ccatgcgcgc ggcgatgcgc gcgaactggt atggcctgct gggcaaaaaa   1020
attaaagata cctttggcca tattggcggc ccgattctgg gcggcctggt gggcctgaaa   1080
aaaccgaaca accatggcgt gccgtatagc ctgaccgaag aatttaccag cgtgtatcgc   1140
atgcatagcc tgattccgag caccctgaaa ctgcgcgatc cgaccggcca gccggatgcg   1200
aacaacagcc cgccgtgcct ggaagatatt gatattggcg aaatgattgg cctgaaaggc   1260
gaagaacagc tgagcaaaat tggctttgaa aaacaggcgc tgagcatggg ctatcaggcg   1320
tgcggcgcgc tggaactgtg gaactatccg agctttttc gcaacctgat tccgcagaac   1380
ctggatggca ccaaccgcag cgatcgcatt gatctggcgg cgctggaagt gtatcgcgat   1440
cgcgaacgca gcgtgccgcg ctataacgaa tttcgccgcc gcctgtttct gattccgatt   1500
aaaagctggg aagatctgac cagcgataaa gatgcgattg aaaccattcg cgcgatttat   1560
ggcgatgatg tggaaaaact ggatctgctg gtgggcctga tggcggaaaa aaaaattaaa   1620
ggctttgcga ttagcgaaac cgcgtttaac attttattc tgatggcgag ccgccgcctg   1680
gaagcggatc gcttttttac cagcaacttt aacgaagaaa cctataccaa aaaaggcatg   1740
cagtgggtga aaaccaccga aggcctgcgc gatgtgatta accgccatta tccggaaatt   1800
accgcgaaat ggatgaaaag cagcagcgcg tttagcgtgt gggatgcgga ttat         1854
```